United States Patent
Scheuringer

(10) Patent No.: US 6,558,897 B2
(45) Date of Patent: May 6, 2003

(54) DEVICE FOR DETERMINING A SUBSTANCE CONTAINED IN A BODY FLUID

(75) Inventor: Kim Scheuringer, Möllersdorf (AT)

(73) Assignee: Care Diagnostica Produktions-und Vertriebsgesellschaft m.b.H., Mollersdorf (AT)

( * ) Notice: Subject to any disclaimer, the term of this patent is extended or adjusted under 35 U.S.C. 154(b) by 61 days.

(21) Appl. No.: 09/866,181

(22) Filed: May 25, 2001

(65) Prior Publication Data

US 2001/0053531 A1 Dec. 20, 2001

(30) Foreign Application Priority Data

Jun. 14, 2000 (DE) ...................... 200 10 628 U

(51) Int. Cl.[7] .............. C12Q 1/00; C12Q 1/37; G01N 33/53; C12M 1/34

(52) U.S. Cl. ............... 435/4; 435/23; 435/7.1; 435/283.1; 435/287.7; 435/287.1; 435/287.2; 422/68.1; 422/50

(58) Field of Search ................. 435/4, 23, 7.1, 435/283.1, 287.7, 287.1, 287.2; 422/68.1, 50

(56) References Cited

U.S. PATENT DOCUMENTS 4,780,283 A * 10/1988 Meinecke et al. ............ 422/68

OTHER PUBLICATIONS

PGPUB Document No. 20010053531, Scheuringer, Kim; Dec. 20, 2001.*

* cited by examiner

Primary Examiner—Louise N. Leary
(74) Attorney, Agent, or Firm—Ladas & Parry

(57) ABSTRACT

A device for determining a substance contained in a body fluid is provided. An indicator member has a testing zone that changes the color based on the concentration level of the substance contained in a body fluid applied to the testing zone. The indicator member is rotatably mounted on a basic carrier. A set of differently colored color fields is provided on the basic carrier along the circumference of a circle having a radius from the center of said basic carrier. The indicator member rotates about the center of said basic carrier. The changed color of said testing zone of said indicator member is compared to said differently colored color fields on the basic carrier.

16 Claims, 1 Drawing Sheet

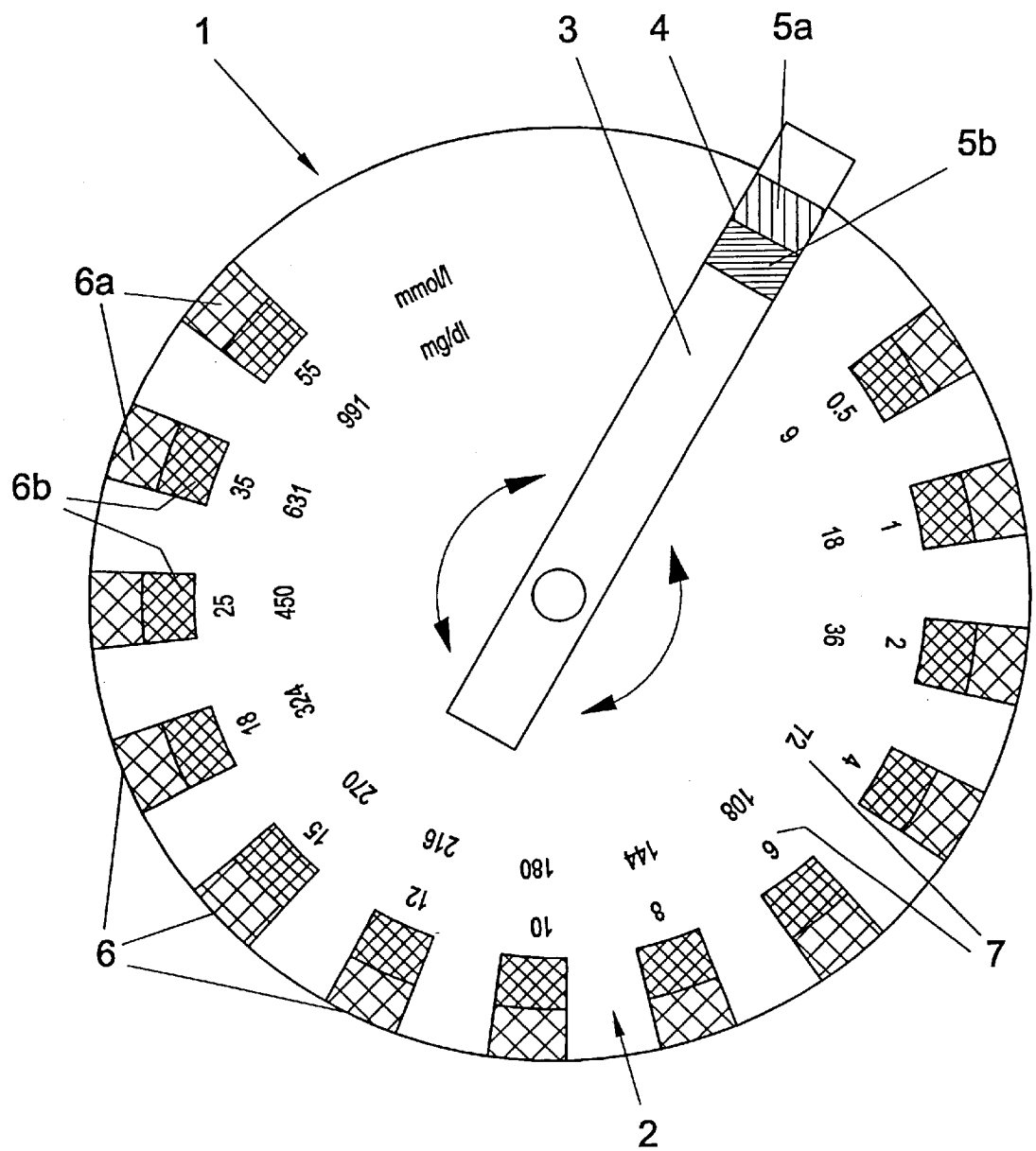
Figure (1)

DEVICE FOR DETERMINING A SUBSTANCE CONTAINED IN A BODY FLUID

FIELD OF THE INVENTION

The invention relates to a device for determining a substance contained in a body fluid, and comprising an indicator member having a testing zone which is coated with a test substance capable of changing its color depending on the substance concentration.

BRIEF DESCRIPTION OF THE BACKGROUND ART

To test the body's health of both (chronically) ill and healthy persons, frequently body liquids are analyzed for certain substances. As a rule, this is carried out directly by a physician or in a laboratory. In doing so, the body fluids, e.g. blood or urine, are tested for the presence and concentrations, respectively, of specific substances, e.g. sugar, hormones, antigens or antibodies.

A testing device is, e.g., described in U.S. Pat. No. 4,748,114 A, where a test strip is provided which changes its color upon the application of blood or urine in dependence on the concentration of glucose. However, this test strip is sent away for the analysis thereof, e.g. to a laboratory or to a physician. To prevent the color change which often occurs already after one to two hours, a membrane is applied to the test strip. Yet due to this application of the membrane, this test strip is relatively complicated and thus expensive to produce, and particularly the necessity of a separate later evaluation is a disadvantage. A daily check is rendered difficult in this manner. Moreover, healthy persons who merely want to carry out a self-check will hardly or rarely use this test since the professional evaluation (by a physician) involves costs and, moreover, numerous persons feel inhibited when they are to consult a doctor.

SUMMARY OF THE INVENTION

Thus, it is an object of the present invention to provide a device for determining a substance contained in a body fluid which overcomes the drawbacks set out above and which allows a test to be carried out at home without professional assistance, with the patient himself/herself, moreover, being able to determine the result.

Furthermore, it is an object of the invention to provide a device which is simple and inexpensive to produce so that it will also be suitable for daily determinations, in particular in the form of a "disposable test" to be used only once.

Moreover, it is an object of the invention to provide a device which allows carrying out the substance determination in a particularly simple manner.

According to this invention, the device comprises an indicator member which is rotatably mounted on a basic carrier; according to a circular line extending about the axis of rotation of the indicator member, differently colored color fields are provided on the basic carrier which have associated corresponding concentration indications of the substance to be determined. By applying the body fluid to the testing zone on the rotatable indicator member, the color of the test substance is changed, the change of color depending on the concentration of the substance to be determined in the body fluid. The per se known test substance applied in the testing zone is specific of the substance to be determined, and any known commercially available test substance may be used. After a short time of reaction which will be different depending on the test substance used, the changing of the color in the testing zone has ended; now, the indicator member may be rotated on the basic carrier, and the test substance of the testing zone comprising the color change is compared to the various color fields on the basic carrier. The color fields are differently colored, each hue being specific of a certain concentration of the substance to be determined. Accordingly, the concentration indication of that color field which has a color corresponding to the color of the test substance can be read, and this will correspond to the concentration of the substance in the body fluid. The present device thus ensures simple handling, and any person can use the device so as to quickly (semi-quantitatively) determine a substance present in a body fluid.

Furthermore, the production of the device is simple and thus inexpensive, thereby rendering it suitable for daily use and as a disposable product.

By information indications as to which concentrations are considered as normal and which are to be considered as too high or too low, an evaluation in a laboratory or by a physician is not necessary since the person himself or herself, when employing the device of the invention, can estimate his/her state of health with the assistance of the result.

The number of color fields on the basic carrier is variable and will also depend on the range of the possible concentration variability of the substance. A relatively higher number of color fields may in each instance ensure a more precise evaluation, since the color fields in this manner will cover a greater number of nuances of the color change.

A further advantage of the device is that in general, very slight amounts of body fluid suffice to carry out the determination; as a rule, one to two drops of body fluid, e.g. blood, will suffice.

To facilitate documentation, the corresponding measuring unit may be provided in addition to the concentration indication, it being, of course, also conceivable to provide several concentration indications for different units per color field, such as, e.g., mmol/l and mg/dl.

In this connection, the testing zone may be provided in that region of the indicator member which is arranged on the radius of the color fields of the basic carrier, which means that by rotation of the indicator member, the testing zone may be positioned immediately adjacent a selected color field so as to directly compare the color change of the test substance with the specific color of the respective color fields. In this manner, it is ensured that also slight color differences can simply be visually registered without any problem.

Advantageously, the indicator member is shaped like the hand of a clock. Thus, the indicator member is rotatably arranged like the hand of a clock along the circular line of the differently colored color fields. The testing zone may be provided over the entire length of the indicator member, yet it is sufficient if merely a strip having a short extension in radial direction, of a few mm, yet preferably over the entire width of the indicator member, is provided. The width of the indicator member may be variable, it is, however, suitable if the indicator member is approximately as wide as a color field or a space between two color fields, so that when comparing the color change of the test substance with a color field, merely a small region of the basic carrier will be hidden and the color fields arranged on either side adjacent the indicator member will be visible.

It is particularly suitable if the basic carrier is disc-shaped, in particular circular-disc-shaped. The center of the circle line of the differently colored color fields thus simultaneously will be the center of the circular disc-shaped basic carrier and the center of rotation of the indicator member, so that the device will resemble the face of a clock.

An advantageous device is provided in that the color fields are arranged at the rim of the circular-disc-shaped basic carrier. In this manner, the space of the basic carrier of a given size will be maximally utilized so that as many color fields as possible with sufficient spacing between the color fields can be provided.

Preferably, the length of the clock-hand-shaped indicator member substantially corresponds to the radius of the circular-disc-shaped basic carrier. If the color fields are arranged at the rim of the basic carrier, it is suitable to provide the testing zone at the end, or close to the end, respectively, of the indicator member; in this manner, the colors of the test substance and the color fields are directly comparable with each other. The clock-hand-shaped indicator member may, however, protrude somewhat beyond the rim of the basic carrier so that it may be gripped for rotation thereof.

Moreover, it is advantageous if two color fields each, corresponding to test substances which change colors differently, are provided and if the indicator member comprises two test substance zones with corresponding test substances that change colors differently. This increases the safety and facilitates the color comparison, respectively, and it may particularly provided for one color field to have a blue hue and a further color field to have a red hue. Since some persons have difficulties differentiating between shades of the series of blue hues and for others the red hue series is a problem, a determination by means of color comparison with this device thus is easy to carry out for all persons.

Preferably, the indicator member comprises a test substance for determining the sugar content of the blood and/or for testing the protein and/or for determining antibodies or antigens and/or for a pregnancy test and/or for a fertility test. The test substances for the different determinations, or tests, respectively, are well known to those skilled in the field of medical analyses. It goes without saying that the concentration indications must be adapted to the test substance, and for each test substance the appropriate body fluid must be applied.

For a particularly simple production it is suitable if the basic carrier is made of cardboard coated by a transparent film of synthetic material. A basic carrier made of cardboard is simple and inexpensive to produce, the film of synthetic material ensuring that the body liquid will not get into direct contact with the cardboard and thus destroy or change the inscription and the color of the color fields, respectively. Since the film of synthetic material is transparent, the inscription of the basic carrier may be applied directly to the cardboard and will be well visible through the transparent film. The film of synthetic material preferably is colorless so that the colors of the color fields will not be changed by the film of synthetic material.

It is furthermore suitable if the indicator member is made of a synthetic material. In this manner, the indicator member will have a certain resistance even after the body fluid has been applied, and the risk of tearing is greatly reduced. Moreover, the body fluid will not be absorbed by the indicator member.

A further aspect of the present invention relates to a method of determining a substance contained in a body fluid by means of a device of the invention as described above, the body fluid being applied to the testing zone of the indicator member such that the test substance present in the testing zone will change its color depending on the substance concentration, whereupon the indicator member will be rotated on the basic carrier so as to compare the test substance of the testing zone which has changed its color with the color fields and to read the concentration indication of the color field corresponding to the color of the test substance. This method can, as mentioned already previously, be carried out particularly simply and quickly, the patient himself/herself being capable of carrying out the test directly at home. Neither trained personnel nor additional apparatus are required therefor.

BRIEF DESCRIPTION OF THE DRAWING

In the following, the invention will be explained in more detail by way of a preferred exemplary embodiment and with reference to the drawing, the single FIGURE of which shows a top view onto the inventive device.

DESCRIPTION OF THE PREFERRED EMBODIMENT

In the FIG. (1), a device 1 for determining a substance contained in a body fluid, in particular blood sugar in blood, is illustrated in a top view; a circular-disc-shaped basic carrier 2 is visible, and in the center of the carrier, an indicator member 3 is rotatably attached. The indicator member 3 has the shape of the hand of a clock and comprises a testing region 4 with two testing zones 5a, 5b near its outer end.

It would, of course, also be possible to provide a polygonal, e.g. square, basic carrier. Likewise, also various shapes are possible for the indicator member, e.g. triangular or pear-shaped indicator members.

The length of the clock-hand-shaped indicator member 3 substantially corresponds to the radius of the circular disc-shaped basic carrier 2, the indicator member 3, however, protruding somewhat beyond the rim of the basic carrier 2 so that it can be gripped for rotation purposes. At the rim of the basic carrier 2, spaced apart color fields 6 are provided corresponding to a circle line extending around the center of rotation of the indicator member 3. The color fields 6 have corresponding associated concentration indications 7 of the substance to be determined. According to this exemplary embodiment, the concentrations in each case are given by two different units. Two color fields 6a, 6b are provided per concentration, the colors of which correspond to the possible colors of the test substances capable of changing colors, of the two testing zones 5a, 5b on the indicator member 3. The color fields 6a of the outer circle line are provided in blue hues, and the color fields 6b of the inner circle lines are provided in red hues. Thus, people who are able to see the red hues—or, on the other hand, the blue hues—more easily, will be able to use the device without any problems.

EXAMPLE

To effect a determination of the sugar content of the blood, one to two drops of blood are applied directly to the testing zone 4 of the indicator member 3. For this purpose, a finger is pricked with a pricking means known per se after having been cleaned, and a sufficient amount of blood is squeezed out so as to completely wet the testing zone 4.

Thirty seconds after application, the residual blood is swabbed off the testing zone, e.g. by means of a clean handkerchief. After sixty seconds, during which the color change develops, the indicator member 3 is rotated on the basic carrier 2 so as to compare the test substance of the testing region 4, or the testing zones 5a, 5b, respectively, exhibiting the color change with the color fields 6a, 6b. The concentration indication corresponding to those color fields 6a, 6b which exhibit the same color as the test substance with the changed colors in the testing zones 5a, 5b, indicates the sugar content of the patient's blood. The sugar content may either be read in mmol/l or in mg/dl, and may be recorded for documentation purposes. Concentrations of between 72 mg/dl (4 mmol/l) and 108 mg/dl (6 mmol/l) are considered as normal levels. If the results are below 72 mg/dl (4 mmol/l) or above 108 mg/dl (6 mmol/l), the blood sugar levels are too low, or too high, respectively, and the patient may draw the consequences therefrom, e.g. see a doctor for carrying out a more precise analysis.

If the device 1 is used for a different determination, the concentration indications must, of course, be adapted accordingly.

What is claimed is:

1. A device for determining a substance contained in a body fluid, said device comprising:

a basic carrier, and an indicator member, said basic carrier mounting said indicator member for rotation movement around the center of rotation of said basic carrier, and said basic carrier being provided with differently colored color fields arranged along the circumference of a circle having a radius about said center of rotation, wherein each color field indicates a concentration level of the substance contained in the body fluid, and said indicator member having a testing zone having testing substance coated thereon, wherein said testing zone is capable of changing the color according to the concentration level of the substance contained in the body fluid to determine the contained substance.

2. The device as set forth in claim 1, wherein said indicator member is shaped like a hand of a clock.

3. The device as set forth in claim 1, wherein said basic carrier is disc-shaped.

4. The device as set forth in claim 3, wherein said basic carrier is circular-disc-shaped.

5. The device as set forth in claim 4, wherein said color fields are provided along the rim of said circular-disc-shaped basic carrier.

6. The device as set forth in claim 5, wherein said indicator member is shaped like a hand of a clock and has a length substantially corresponding to the radius of said circular-disc-shaped basic carrier.

7. The device as set forth in claim 1, wherein two color fields of testing substances capable of differently changing their colors are provided on said basic carrier for each concentration of said body-fluid-contained substance, two testing zones with testing substances accordingly capable of differently changing their colors for a respective concentration being provided on said indicator member.

8. The device as set forth in claim 1, wherein said testing substance provided on said indicator member is a testing substance for a blood sugar content determination.

9. The device as set forth in claim 1, wherein said testing substance provided on said indicator member is a testing substance for a protein test.

10. The device as set forth in claim 1, wherein said testing substance provided on said indicator member is a testing substance for determining antibodies.

11. The device as set forth in claim 1, wherein said testing substance provided on said indicator member is a testing substance for determining antigens.

12. The device as set forth in claim 1, wherein said testing substance provided on said indicator member is a testing substance for a pregnancy test.

13. The device as set forth in claim 1, wherein said testing substance provided on said indicator member is a testing substance for a fertility test.

14. The device as set forth in claim 1, wherein said basic carrier is made of cardboard coated with a transparent film of a synthetic material.

15. The device as set forth in claim 1, wherein said indicator member is made of a synthetic material.

16. A method of determining a substance contained in a body fluid according to the concentration level of the substance in the body fluid by means of a device including a basic carrier having different color fields provided about its circumference and associated concentration indications, and an indicator member rotatably mounted on said basic carrier about the center of rotation of said basic carrier, said indicator member including a testing zone capable of changing its color according to the concentration level of the substance contained in the body fluid applied to said testing zone, said method comprising:

applying said body fluid to said testing zone of said indicator member so as to change the color of said testing substance in said testing zone according to the concentration level of substance contained in the body fluid; and subsequently rotating said indicator member about said center of rotation of said basic carrier to compare the changed color of said testing zone to one of said color fields on said basic carrier to read the associated concentration indication of the color field on said basic carrier corresponding to said changed color of said testing substance.

* * * * *